(12) United States Patent
Altman

(10) Patent No.: US 7,951,115 B2
(45) Date of Patent: *May 31, 2011

(54) SAFETY DIALYSIS NEEDLE/CATHETER SYSTEM AND METHOD OF USE

(76) Inventor: Sanford D. Altman, North Miami Beach, FL (US)

( * ) Notice: Subject to any disclaimer, the term of this patent is extended or adjusted under 35 U.S.C. 154(b) by 550 days.

This patent is subject to a terminal disclaimer.

(21) Appl. No.: 12/036,457

(22) Filed: Feb. 25, 2008

(65) Prior Publication Data

US 2008/0195046 A1   Aug. 14, 2008

Related U.S. Application Data

(63) Continuation-in-part of application No. 10/685,546, filed on Oct. 14, 2003, now Pat. No. 7,335,187.

(51) Int. Cl.
*A61M 5/178* (2006.01)

(52) U.S. Cl. .................... 604/164.01; 604/110

(58) Field of Classification Search ................ 604/110, 604/111, 263, 264, 174, 272, 164.08, 117, 604/189, 523, 506, 531, 532, 95.05; 600/585
See application file for complete search history.

(56) References Cited

U.S. PATENT DOCUMENTS

| | | | |
|---|---|---|---|
| 4,411,655 A | 10/1983 | Schreck | |
| 4,665,906 A | 5/1987 | Jervis | |
| 4,681,570 A * | 7/1987 | Dalton | 604/524 |
| 4,929,241 A | 5/1990 | Kulli | |
| 5,154,699 A | 10/1992 | Ryan | |
| 5,176,655 A | 1/1993 | McCormick et al. | |
| 5,207,644 A | 5/1993 | Strecker | |
| 5,215,525 A | 6/1993 | Sturman | |
| 5,403,283 A | 4/1995 | Luther | |
| 5,407,431 A | 4/1995 | Botich et al. | |
| 5,487,734 A | 1/1996 | Thorne et al. | |
| 5,545,146 A | 8/1996 | Ishak | |
| 5,573,510 A | 11/1996 | Isaacson | |
| 5,578,053 A | 11/1996 | Yoon et al. | |
| 5,645,558 A | 7/1997 | Horton | |
| 5,665,072 A | 9/1997 | Yoon | |
| 5,693,030 A | 12/1997 | Lee et al. | |
| 5,702,367 A | 12/1997 | Cover et al. | |
| 5,704,917 A | 1/1998 | Utterberg | |

(Continued)

FOREIGN PATENT DOCUMENTS

DE   44 34 567   4/1995

OTHER PUBLICATIONS

Lendelein, A. et al. (2001) "AB-polymer networks based on oligo(ε-caprolactone) segments showing shape-memory properties." *PNAS*. vol. 98, No. 3, pp. 842-847.

*Primary Examiner* — Christopher D Koharski
(74) *Attorney, Agent, or Firm* — Saliwanchik, Lloyd & Eisenschenk

(57) ABSTRACT

The present invention provides a safety needle/catheter system and method of use for dialysis procedures. The invention includes a safety feature that prevents inadvertent needle sticks by administrators. The invention further includes a catheter portion composed of shape memory materials. The catheter portion has a deformed shape and size that facilitates insertion of the catheter portion and closure of the catheter incision and a recovered shape and size that can reduce the severity of infection and/or clotting, as well as provide improved maintenance and control over proper fluid volume flow during dialysis.

15 Claims, 2 Drawing Sheets

U.S. PATENT DOCUMENTS

| | | | |
|---|---|---|---|
| 5,743,891 A | 4/1998 | Tolkoff et al. | |
| 5,853,394 A | 12/1998 | Tolkoff et al. | |
| 5,911,705 A | 6/1999 | Howell | |
| 5,964,744 A * | 10/1999 | Balbierz et al. | 604/530 |
| 5,971,959 A | 10/1999 | Liu | |
| 5,997,507 A | 12/1999 | Dysarz | |
| 6,056,726 A | 5/2000 | Isaacson | |
| 6,077,244 A | 6/2000 | Botich et al. | |
| 6,117,110 A | 9/2000 | Radmand | |
| 6,238,383 B1 | 5/2001 | Karram et al. | |
| 6,261,311 B1 | 7/2001 | Sharkey et al. | |
| 6,398,743 B1 * | 6/2002 | Halseth et al. | 600/585 |
| 6,436,070 B1 | 8/2002 | Botich et al. | |
| 6,461,362 B1 | 10/2002 | Halseth et al. | |
| 6,475,189 B1 | 11/2002 | Lilley, Jr. | |
| 6,605,061 B2 | 8/2003 | VanTassel et al. | |
| 6,622,731 B2 | 9/2003 | Daniel et al. | |
| 7,335,187 B2 * | 2/2008 | Altman | 604/164.08 |
| 2002/0091352 A1 | 7/2002 | McGuckin, Jr. et al. | |
| 2002/0107483 A1 | 8/2002 | Cook | |
| 2002/0115964 A1 | 8/2002 | Boudreaux | |
| 2002/0123723 A1 | 9/2002 | Sorenson et al. | |
| 2002/0147427 A1 | 10/2002 | Chang | |
| 2002/0161338 A1 | 10/2002 | Peterson | |
| 2002/0177866 A1 | 11/2002 | Weikel et al. | |
| 2004/0193109 A1 | 9/2004 | Prestidge et al. | |

\* cited by examiner

SAFETY DIALYSIS NEEDLE/CATHETER SYSTEM AND METHOD OF USE

CROSS-REFERENCE TO A RELATED APPLICATION

This application is a continuation-in-part application of U.S. application Ser. No. 10/685,546, filed Oct. 14, 2003 now U.S. Pat. No. 7,335,187, which is incorporated herein it its entirety.

BACKGROUND OF INVENTION

It is estimated that the prevalence of chronic kidney disease in the United States population is 11% (roughly 19.2 million adult individuals) and increasing. The kidneys are organs which function to extract water and urea, mineral salts, toxins, and other waste products from the blood. Patients having one or both defective kidneys often require artificial "dialysis," a procedure that simulates the function of the kidneys in cleaning wastes from the blood.

There are currently two forms of dialysis available: hemodialysis and peritoneal dialysis. Hemodialysis is a well-known method of providing renal (kidney) function by using a machine to clean wastes and extra fluids from blood and to re-circulate the cleansed blood back into the patient's body. In hemodialysis procedures, blood is withdrawn from the patient's body through an access to a dialysis machine, also commonly referred to as a kidney (or dialysis) machine. In the dialysis machine, toxins and other waste products diffuse through a semi-permeable membrane into a dialysis fluid closely matching the chemical composition of the blood. The filtered blood (i.e., blood with the waste products removed) is then returned to the patient's body. As can be appreciated, proper access to the patient's blood and transport of the blood to and from the dialysis machine for this extended period of time is critical to hemodialysis.

A hemodialysis access (or vascular access) is a large diameter, fast flowing conduit that is located just beneath the skin surface. The superficially located, large diameter, and fast flow conduit/access is typically stuck three times per week with two needles, wherein one needle removes blood from the patient's body and the second needle returns cleansed blood to the patient's body. The blood goes through the dialysis machine and through a special filter called a dialyzer. A patient can receive hemodialysis treatment through either a catheter, graft, or fistula.

A catheter is a temporary access which consists of a tube placed directly into a large vein. With hemodialysis treatment, a catheter is connected directly to a dialysis machine and does not require the use of needles. The catheter may be a single tube with two separate lumens or two separate tubes.

Approximately 70% to 80% of patients in the United States receive hemodialysis through either a fistula or a graft. A fistula is a permanent access that is created when a vein is connected to an artery, usually in a patient's extremity. By directly connecting the vein to the artery, the vein receives "high" or "arterial-like" flow. This results in enlargement in the diameter of the vein to form a "fistula."

A graft is also a permanent access that is created by a piece of synthetic material (i.e., DACRON) joined from an artery to a vein. This synthetic material is located superficially under the skin and is of adequate diameter for use as a hemodialysis conduit/access.

Despite advances that have been made in providing vascular access for dialysis, few advances have been seen in needles that have been used to cannulate these accesses. Needles used in dialysis are generally 14-17 gauge needles made of stiff material (i.e., metal), have a single end hole, are 1 to 1.5 inches in length, and may or may not include a safety feature to prevent needle sticks. There are a variety of problems associated with currently available needles. Because surgically-created accesses are often deeply positioned, it can be difficult to introduce a needle of only 1 to 1.5 inches in length to the access. Further, due to their shortness in length, current needles will often "back out" of an access during dialysis procedures, which causes returning blood to flow into subcutaneous tissue rather than into the vascular system as intended.

In addition, current needles are generally tubular in shape. Due to their shape and stiffness, current dialysis needles do not have a means for securing their position in the access and will often slide easily out to interrupt hemodialysis treatments. Further, their shape and stiffness often cause posterior access wall punctures. This may damage the graft, fistula, or extremity that is being used for dialysis.

Further, by using needles with a single end hole, the pressure/sheer stress of returning blood (or delivering dialysate fluid) through the single end hole is great. This may cause disruption in blood cell morphology as well as damage to cells lining the graft or fistula. To compensate for this, dialysis needles often have large diameters. Unfortunately, large needle profiles impede insertion of the needle and closure of the needle site. Moreover, for certain individuals, large needles with single end holes lack the ability to efficiently maintain proper flow of fluid volume for effective dialysis.

A further disadvantage of current dialysis needles is the risk involved to administering personnel with inadvertent needle-stick experiences. A substantial risk is present to the administering personnel as dialysis needles are inserted into and removed from a patient for dialysis. Inserted needles can come into contact with bodily fluids that may contain infectious, microbiological agents. Common dangerous blood-borne pathogens include HIV and hepatitis, which have the capability of infecting an individual through an inadvertent needle stick.

Thus, use of current dialysis needles can cause much pain and expense to both the patient and administrator. For example, hemodialysis patients with a surgically-created vascular access (i.e., graft or fistula) often develop bruises due to misplaced needles (infiltration). The risk of infiltration is frequently related to difficult cannulation, deep position of graft or fistula, and/or needle migration during dialysis. Moreover, should the access be damaged, further surgery may be required to provide a new access for dialysis.

Approaches currently available to remedy the risk of needle sticks include those disclosed by Sorenson et al. (U.S. patent application No. 2002/0123723), Tolkoff et al. (U.S. Pat. No. 5,743,891), and Lee et al. (U.S. Pat. No. 5,693,030). These apparatuses provide a means of preventing needle sticks upon insertion and retraction of a needle from a patient. However, inability to control and provide proper fluid flow through a needle that would function for effective dialysis as well as the risk of infection and clotting are still problems associated with the above-referenced safety needles.

Recent advancements in the development of biocompatible shape-memory materials are particularly germane to expanding the ability of current dialysis needle technology to allow for prevention of needle migration and posterior access wall puncture, as well as to provide optimal fluid exchange. Shape-memory polymers and alloys, in particular, have been investigated for certain medical applications, namely stents, sutures, and closing plugs. These polymers or alloys were developed to have one shape at one condition (i.e., low temperature) and another shape at a second condition (i.e., high temperature).

Hence, despite the availability of the above needles and safety needles, there is a continuing need for an improved dialysis needle that prevents potential needle stick experiences while facilitating dialysis, helping to secure the needle during dialysis to prevent needle migration and/or dislodgement, reducing sheer stress of blood flow, and reducing the risk of other complications associated with dialysis procedures.

BRIEF SUMMARY

The present invention provides a unique safety needle/catheter for use during dialysis. By combining a safety needle feature with a pre-shaped catheter containing at least one aperture for optimal fluid exchange, the present invention improves dialysis while reducing the risk of needle sticks, the risk of needle migration or withdrawal, the risk of posterior access wall puncture, the risk of infiltration and cell damage, and the amount of sheer stress generally associated with current dialysis needles.

The safety needle/catheter of the invention includes a safety feature to prevent inadvertent needle sticks to administering personnel. The invention further includes a catheter portion composed of a shape memory material having an original shape that can decrease the risk of infiltration and/or disengagement of the needle from the access as well as provide improved maintenance and control over proper fluid volume flow during dialysis.

In an embodiment, the invention provides a needle/catheter that reduces the severity of infection and/or clotting by incorporating anti-infectious and/or anti-clotting agents or compositions in or around the surface of the catheter portion.

In a preferred embodiment, the safety needle/catheter system includes a catheter portion composed of shape memory materials, a movable penetrating needle for creating an entrance through subcutaneous tissue to a target site, and a safety feature designed to render the needle harmless. In one embodiment, the safety feature includes a needle guard that shields the needle from administering personnel after needle penetration.

In another embodiment, the safety feature includes means for retracting the needle into a housing to prevent inadvertent contact with the needle by administering personnel.

In a preferred embodiment, the safety feature includes a housing, a biasing element, and a needle retainer. In accordance with the present invention, the catheter portion is mounted on the housing. The movable penetrating needle is operable between an extended position extending forward of the distal end of the catheter portion and a retracted position in which the needle is enclosed in the housing. The biasing element biases the needle toward the retracted position and the needle retainer releasable retains the needle in the extended position against the bias on the biasing element. Upon placement of the needle/catheter at a target site, the needle retainer is deactivated to release the needle for retraction into the housing and to decrease the risk of inadvertent needle sticks by administering personnel.

According to the present invention, shape memory materials are suitable for forming a catheter portion because of their ability to return to some previously defined shape or size when subjected to the appropriate condition (i.e., temperature). Moreover, commonly available shape memory polymers and alloys can be easily processed and demonstrate ease of shaping, high shape stability, adjustable transition temperatures, and excellent biocompatibility.

In one embodiment, the catheter portion composed of shape memory materials is molded to a shape and size suitable for providing optimal fluid volume flow during dialysis procedures while also providing conditions under which less clotting, tissue irritation, infection, or migration and/or disengagement of the catheter portion will occur. The molded catheter portion is then deformed to a size and shape (i.e., small outer diameter catheter body) that facilitate insertion of the catheter portion and closure of the catheter incision.

In another embodiment, the condition for defining the shape of the shape memory materials is temperature-based. The deformation of the catheter portion is performed above the shape recovery temperature of the polymer and is then cooled to fix the catheter portion to the deformed decreased-size shape. Thus, the small diameter catheter portion is easily inserted into the patient at a desired location in the body and is then warmed by the body to above the shape memory temperature to recover the original shape suitable for proper fluid flow.

The catheter portion according to the present invention has at least one opening to enable fluid flow. In a further embodiment, the original shape (i.e., shape recovered at body temperature) is in the form of a helical coil, sinusoidal wave, bolous, loop, pig tail, tennis racquet, halo, or mushroom. In a preferred embodiment, the catheter portion includes a plurality of openings and is tapered at the distal end.

More preferably, the distal end of the catheter portion forms at least one loop (such as a helical spiral, a pig tail, or sinusoidal wave), wherein within each loop there are a multitude of openings positioned such that they face inwardly toward the inside surface of the loop. Positioning the openings in such a fashion advantageously reduces the chance of infection, extravasation, or embolism/clot formation due to displaced plaque during dialysis.

According to the present invention, the shape memory material of the catheter portion can incorporate or be treated with at least one therapeutic agent or surface material. Contemplated therapeutic agents include, but are not limited to, anticoagulants, human growth hormone, and anti-infectious agents. Contemplated surface materials include, but are not limited to, hydrophilic coatings (i.e., hydrogels) to increase lubricity and facilitate insertion of the catheter portion.

The present invention provides a unique needle/catheter and safety features to easily cannulate a hemodialysis access, to decrease catheter migration and/or withdrawal from the access, to enable maintenance and control of proper fluid volume flow while decreasing the likelihood of clotting and infection during dialysis, and to protect administrators from inadvertent needle sticks. Safety features for needles, including their methods for preparation, which can be applied to the present invention, are described in numerous patents and patent applications, including U.S. Pat. Nos. 6,436,070, 6,398,743; 6,077,244, 5,997,507, 5,743,891; 5,665,073; 5,407,431; 5,403,283, and 4,929,241 and U.S. Patent Application Ser. Nos. 2002/0115964 and 2002/0107483.

The safety dialysis needle/catheter system in accordance with the present generally includes a catheter portion formed of a shape memory material, a movable penetrating needle, and safety feature to render the needle harmless from inadvertent needle sticks. In a preferred embodiment, a safety needle/catheter system includes a catheter portion, a penetrating needle, a housing/lure lock having a flange, a stop, a manual retraction button, and a concentric coil spring. The concentric coil spring is compressed against the flange of the housing/lure lock. The flange provides a clamping means for stabilizing the catheter portion and the needle. The spring coil is retained within the catheter portion and against the housing/lure lock by a stop that is cantilevered from the housing/lure lock. This cantilevered stop also includes a conveniently located button that may be easily depressed by a finger of one hand holding the housing/lure lock. Depression of the button retracts the needle into the housing/lure lock. For example, after the needle and catheter portion have been properly inserted into a patient, the button is activated allowing the spring to force the needle to the proximal end of the housing/lure lock. As a result, the sharp distal tip of the needle is withdrawn from within the catheter portion and placed out of reach of the administrating personnel.

The distal end of the catheter portion can form a variety of shapes once the penetration needle is retracted. In one embodiment, the distal end of the catheter portion is made of a shape memory polymer or alloy having a shape recovery temperature in the range of 20° C. to 70° C., preferably in the range of 30° C. to 50° C. because of the relation to body temperature. By way of example, the shape memory alloy or polymer allows for the distal end of the catheter portion to remain relatively linear for ease of insertion (i.e., when the shape recovery temperature is lower than 20° C.). When the shape recovery temperature is between 30° C. and 50° C., (i.e., after insertion into the body), the original shape of the alloy or polymer (i.e., a spiral or loop) will be formed in the body of the patient. In an embodiment, the distal end of the catheter portion is tapered and includes a multitude of openings.

In a method of use, a penetrating needle of the invention is inserted into subcutaneous tissue to create an entrance to a target site and to allow a catheter portion to advance through the entrance to the target site. The penetrating needle is of sufficient length and appropriate shape to easily infiltrate a hemodialysis access. Once the needle creates an entrance to a target site and the catheter portion is advanced through the entrance to the target site (i.e., fistula, graft, or abdominal cavity), the safety feature is engaged to render the needle harmless. The catheter portion is preferably formed of a shape memory material. Thus, the catheter portion can be formed of an original shape that provides proper fluid volume flow and/or reduces the risk of clotting and/or infection. The catheter portion can then be deformed into a shape and size that would facilitate catheter portion insertion and closure of the incision. When the catheter portion has advanced through the entrance and is placed at a target site, the catheter portion will be presented with an appropriate condition for shape recovery (i.e., body temperature). According to the present invention, the catheter portion will form an original shape at the target site that will provide proper fluid volume flow for dialysis procedures and/or decrease the likelihood of infection and clot formation during dialysis.

It is envisioned that the subject invention will advantageously allow graft or fistula hemodialysis to be delivered through a catheter portion rather than a needle to lower the risk of infiltration, reduce the pressure/sheer stress of returning blood by returning blood through multiple side holes, and better intraluminal positioning and access. Further, the subject safety needle/catheter system can be used in peritoneal dialysis.

DETAILED DISCLOSURE

Figure 1:
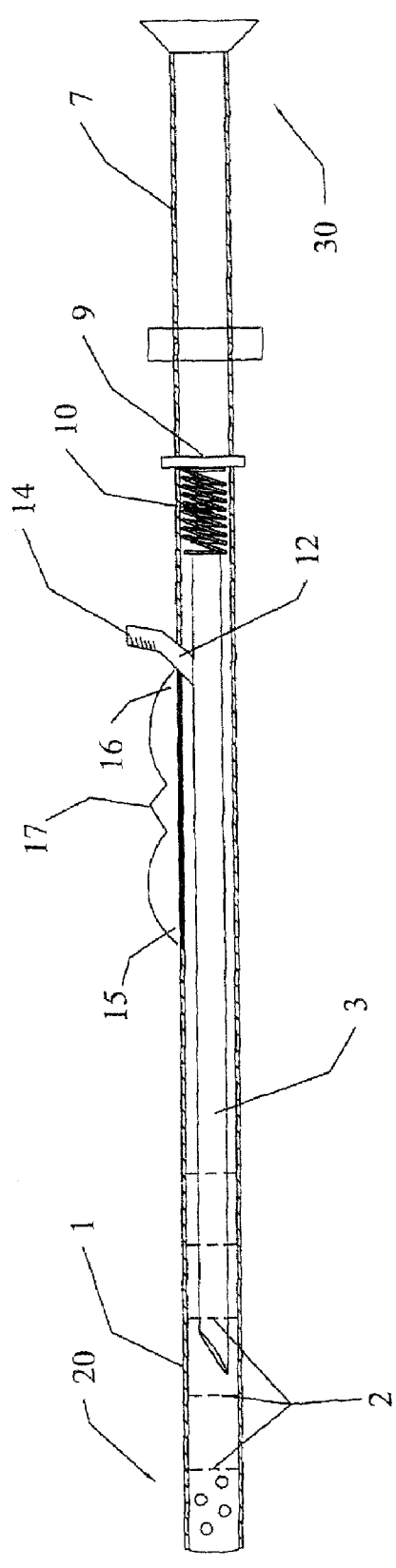
FIG. 1 shows the basic shape of a safety needle/catheter assembly according to the subject invention.

The present invention provides a unique safety needle/catheter system for use during dialysis and methods for using the safety needle/catheter system. The invention includes a safety feature that prevents inadvertent needle sticks to administering personnel. The invention further provides a catheter portion composed of a shape memory material having an original shape that can decrease the risk of infiltration and/or disengagement of the needle from the access, reduce the severity of infection and/or clotting, as well as provide improved maintenance and control over proper fluid volume flow during dialysis.

Definitions

As used herein, the term "biocompatible" refers to the property of being compatible with and having no significant toxic, injurious, or immunological effect on living tissue:

As used herein, the term "shape memory" refers to the ability to return to some previously defined shape or size when subjected to an appropriate condition (i.e., thermal procedure, stress).

Unless specifically otherwise disclosed or taught, materials for making components of the present invention may be selected from appropriate materials such as metal, metallic alloys, natural and manmade fibers, vinyls, plastics and the like, and appropriate manufacturing or production methods including casting, extruding, molding and machining may be used.

Catheters

The present invention provides a safety needle/catheter system with structural designs that reduce the likelihood of infiltration and/or disengagement of the needle from the access, decrease the tendency of catheter crimping while also achieving high fluid volume flow rates without compromising the maximal catheter outer diameter. The catheter portion of the system of the invention can be produced and formed in a wide range of shapes and sizes appropriate for dialysis procedures. Contemplated catheter portions of the invention can be transparent or opaque, and include features such as visible markers along the body of the catheter portion to indicate the distance from the most proximal end of the catheter to the surface of the skin. Such markers aid the user in assessing whether the catheter portion is appropriately engaged at a target site (i.e., fistula).

The catheter portion of the invention can be composed of materials commonly used in the manufacture of catheters including, but not limited to, conventional flexible materials such as polyolefins (i.e., polyethylene (PE), polypropylene (PP), ethylenepolypropylene copolymer), polyvinyl chloride (PVC), polyamide, polyurethane, polyester, fluorine resin (i.e., polytetrafluoroethylene (PTFE), tetrafluoroethylene hexafluoropropylene copolymer (FEP)), silicone rubber. As provided below, certain embodiments of the invention have catheter portions composed of shape memory materials, including those commercially known as "nickel-titanium," "titanium-nickel," "Tee-nne," "Memorite," "Nitinol," "Tinel," and "Flexon." The catheter portion designs of the present invention apply equally to single lumen, double lumen, and multiple lumen embodiments.

Shape Memory Catheters

Shape memory materials have unique attributes, which make them an ideal candidate for many biomedical applications. According to the present invention, shape memory materials are suitable for forming a catheter portion of the invention because of their ability to return to some previously defined shape or size when subjected to the appropriate condition (i.e., temperature). Moreover, commonly available shape memory polymers and alloys can be easily processed and demonstrate ease of shaping, high shape stability, adjustable transition temperatures, and excellent biocompatibility. One skilled in the art would readily understand how to apply such shape memory polymers and alloys to creating a catheter portion of the subject invention.

Preferred shape memory catheter portions are those composed of biocompatible shape memory alloys or polymers, such as nickel-titanium alloys (i.e., NiTi), copper-base alloys (i.e., CuZnAl and CuAlNi), iron-based alloys (i.e., FePt, FePd, FeNiCoTi, FeNiC, FeMnSi, and FeMnSiCrNi), polymers such as polynorbornene, styrene-butadiene copolymer, polyurethane, or transpolyisoprene; as well as polymer networks based on oligo($\epsilon$-caprolactone) dimethacrylate as crosslinker and n-butyl acrylate as a comonomer. Shape memory materials, including their methods for preparation, that can be used in the present invention are described in numerous patents and publications including, but not limited to, those disclosed in U.S. Pat. Nos. 4,411,655, 4,665,906, and 5,645,558 and in Lendlein, A. et al., "AB-polymer networks based on oligo($\epsilon$-caprolactone) segments showing shape-memory properties," *PNAS*, 98:3, 842-847 (2001).

The catheter portion of the present invention can be of any catheter gauge size and/or catheter length appropriate for dialysis procedures. In a preferred embodiment, the catheter gauge size is between 14 and 17 and the catheter length is from about 2 cm in length to about 10 cm in length.

In an embodiment, a catheter portion is formed of shape memory material that exhibits shape recovery. The catheter portion is molded to an original shape and size suitable for optimal fluid volume flow during dialysis procedures. The shape of the catheter portion is then deformed from its original shape to a shape suitable for ease of introduction into a body. Once introduced into an access, the catheter portion resumes its original shape to provide optimal fluid volume flow and prevent migration and/or withdrawal from the access and/or prevent puncture of poster access wall by the catheter. When the catheter portion is to be withdrawn from the patient, the catheter portion resumes its deformed shape to allow for ease of withdrawal of the catheter portion.

In another embodiment, a catheter portion of the invention is formed of shape memory material that exhibits shape recovery when subjected to an appropriate thermal procedure. The catheter portion is molded to an original shape and size suitable for providing optimal fluid volume flow during dialysis procedures as well as providing conditions under which less clotting, tissue irritation, infection, or migration and/or disengagement of the catheter portion will occur. The shape of the catheter portion is deformed from its original shape into a substantially linear shape for ease of introduction into the patient (i.e., small outer diameter catheter body) to facilitate insertion of the catheter portion and closure of the catheter incision. The deformation of the catheter portion is performed above the shape recovery temperature of the polymer/alloy and is then cooled to fix the catheter portion to the deformed decreased-size shape. Thus, the small diameter catheter is easily inserted into the patient at a desired location in the body and is then warmed by the body to above the shape memory temperature to recover the original shape suitable for proper fluid flow and for securing the catheter portion within the access.

In a preferred embodiment, the distal end of the catheter portion is made of a shape memory polymer or alloy having a shape recovery temperature in the range of 20° C. to 70° C., preferably in the range of 30° C. to 50° C. because of the relation to body temperature. By way of example, the shape memory alloy or polymer allows for the distal end of the catheter portion to remain relatively linear for ease of insertion (i.e., when the shape recovery temperature is lower than 20° C.). When the shape recovery temperature is between 30° C. and 50° C., (i.e., after insertion into the body), the preset shape of the alloy or polymer (i.e., a spiral or loop) will be formed in the body of the patient. In an embodiment, the distal end of the catheter portion is tapered and includes a multitude of openings.

In a further embodiment, the original shape (i.e., shape recovered at body temperature) is in the form of a spiral, sinusoidal wave, bolous, loop, pig tail, tennis racquet, halo, or mushroom. In a preferred embodiment, the catheter portion includes a multitude of openings and is tapered at the distal end.

According to the present invention, the shape memory material of the catheter portion can incorporate or be coated with at least one therapeutic agent and/or at least one surface material. Contemplated therapeutic agents include anticoagulants, human growth hormone, and anti-infectious agents. Contemplated surface materials include hydrophilic coatings (i.e., hydrogels) to increase lubricity and facilitate insertion of the catheter portion.

Safety Feature

The present invention combines a unique needle/catheter system with various safety features to protect administrators from inadvertent needle sticks as well as to enable maintenance and control of proper fluid volume flow during dialysis. Safety features for needle/catheters, including their methods for preparation, which can be applied to the present invention, are described in numerous patents and patent applications, including U.S. Pat. Nos. 6,436,070, 6,398,743; 6,077,244, 5,997,507, 5,743,891; 5,665,073; 5,407,431; 5,403,283, and 4,929,241 and U.S. Patent Application Serial Nos. 2002/0115964 and 2002/0107483.

Needle Guard

One embodiment of the present invention provides a hollow catheter portion composed of shape memory material, a movable penetrating needle concentrically retained within the catheter portion, and a safety feature that is a needle guard. The penetrating needle can be disposed in the catheter portion such that the portion of the needle used to create an entrance through the subcutaneous tissue to a target site extends beyond the distal end of the catheter portion. The needle guard can include a means for engaging the needle and a shield that covers the needle upon its withdrawal from the catheter portion.

Retractable Needle

In another embodiment, the safety dialysis needle/catheter system includes a hollow catheter portion composed of shape memory material, a movable penetrating needle concentrically retained within the catheter portion, a housing, a biasing element, and a needle retainer. In accordance with the present invention, the catheter portion is mounted on the housing. The movable penetrating needle retained within the catheter portion is operable between an extended position extending forward of the distal end of the catheter portion and a retracted position in which the needle is enclosed in the housing. The biasing element biases the needle toward the retracted position and the needle retainer releasable retains the needle in the extended position against the bias on the biasing element. Upon placement of the catheter portion at a target site, the needle retainer is deactivated to release the needle for retraction into the housing and to decrease the risk of inadvertent needle sticks by administering personnel.

The needle, in accordance with the present invention, is of sufficient length and appropriate shape to easily infiltrate a hemodialysis access. Such needles are readily apparent to those skilled in the art. In a preferred embodiment, the needle measures from roughly 2 cm to 10 cm in length.

EXAMPLES

The safety dialysis needle/catheter system, as illustrated in FIG. 1, includes a catheter portion 1, a penetrating needle 3, and a housing 7. Catheter portion 1, according to the present invention, is composed of a shape memory material and is hollow to serves as a sleeve for an inner penetrating needle 3.

At times, it might be necessary for the administering personnel inserting the catheter portion into a patient to see that the penetrating needle tip and the catheter portion have reached a desired blood vessel in order to stop advancing the needle tip. Thus, the catheter portion 1 can be designed so that it is transparent and includes at least one marker 2 along the body. Accordingly, the visibility of fluid flow into the catheter portion indicates to the administering personnel that the needle has reached the desired blood vessel.

The penetrating needle 3 is movable relative to the catheter portion 1 and housing 7 between an extended rest position and a retracted position. The needle is movable between an extended position where a distal end of the needle 3 protrudes from the distal end 20 of the catheter portion 1 and a retracted position with the needle 3 safely retained in the housing 7. The safety dialysis system also includes a retracting means 10 for moving the needle from the needle extended position to the needle retracted position. Retracting means 10 can include compression springs, tension springs, torsion springs, pan springs, leaf springs, rubber, plastic or magnets. A means for manually locking the needle 12 from the needle retracted position to the needle extended position that is cantilevered from the housing 7 and can include a convenient button 14. The locking means 12 can include a clamp, twist or other mechanism to allow for the safe retraction of the needle. The button 14 can easily be depressed by a finger of one hand holding the housing 7 to trigger the retracting means 10 to pull the needle into the retracted position.

In a preferred embodiment, the penetrating needle 3 has a sharp distal end. The retracting means 10 is a concentric coil spring compressed against a flange of a housing 7 that provides a clamping means 9 for stabilizing the catheter portion 1 and the needle 3. The spring coil is retained within the catheter portion 1 compressed between the housing 7 and the needle 3. The spring is locked into an extended position by a stop 12, which is cantilevered from the housing 7/lure lock 17. The cantilevered stop 12 includes a convenient button 14 that is easily depressed by a finger of one hand holding the housing 7. By locking the spring into an extended position, the penetrating needle 3 is disposed forward the catheter portion 1 to allow for penetration into a patient. After the penetrating needle 3 and catheter portion 1 have been properly inserted into a patient, the button 14 is manually activated to allow the spring to force the needle 3 to the proximal end 30 of the housing 7. As a result, the sharp distal tip of the needle 3 is withdrawn into the housing 1 out of reach of the administering personnel.

Figure 2:
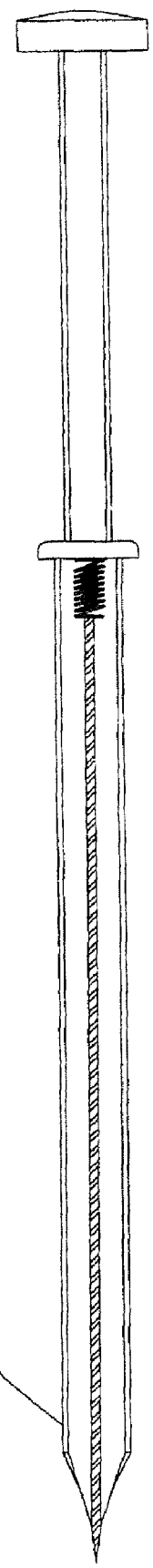
FIG. 2 illustrates the deformed shape of the catheter portion prior to insertion into an individual.

According to the present invention, the distal end of the catheter portion 1 can be deformed in a shape and size that facilitates catheter portion insertion and closing of incision site. For example, as illustrated in FIG. 2, the distal end of the catheter portion 1 can of substantially elongate, linear shape, wherein the distal end of the catheter portion 1 is tapered and includes a multitude of openings. In a preferred embodiment, the catheter portion is deformed to have a small diameter and sharp, tapered distal end.

Figure 3:
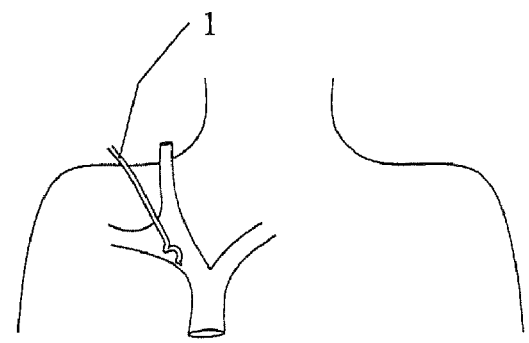
FIG. 3 illustrates the recovered shape of the catheter portion after insertion into an individual.

Once the distal end of the catheter portion 1 is placed in an appropriate condition for recovering an original shape (i.e., body temperature), the distal end of the catheter portion 1 can recover its original shape. By way of example, as illustrated in FIG. 3, when the distal end of the catheter portion 1 is subjected to the appropriate condition for shape recovery, the distal end of the catheter portion 1 may recover a shape wherein the catheter portion remains substantially elongate and linear yet the diameter of the lumen is greater to allow for appropriate fluid volume flow.

Figure 4:
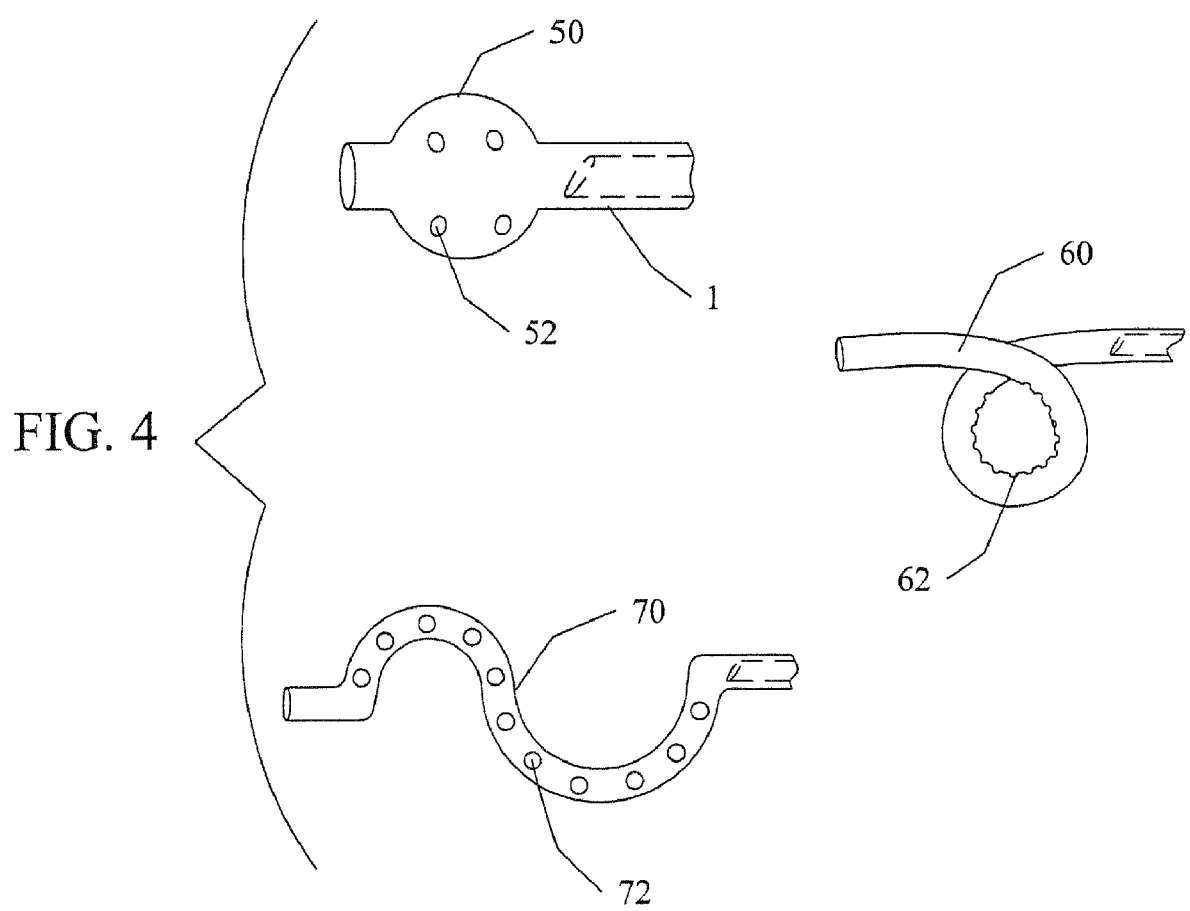
FIG. 4 illustrates exemplary recovery shapes of the catheter portion contemplated by the present invention.

FIG. 4 illustrates examples of other shapes the distal end of a catheter portion 1 can recover when placed in the appropriate condition for shape recovery. In one embodiment, the distal end of the catheter portion 1 forms a bolous 50 that includes at least one opening 52. In another embodiment, the distal end of the catheter portion 1 forms a loop 60 with a multitude of openings 62 within the loop 60. A further embodiment provides a catheter portion 1 having a distal end that forms a sinusoidal shape 70 having a multitude of openings 72 therein.

In a preferred embodiment, the distal end of the catheter portion 1 forms at least one loop 60 (such as a helical spiral, a pig tail, or sinusoidal wave), wherein within each loop there are a multitude of openings 62 positioned such that they face inwardly toward the inside surface of the loop. The positioning of these openings 62 to face inwardly directs fluid flow towards the center of the target site (such as a fistula, graft, or abdominal cavity) where the blood absorbs the energy of the stream of fluid flow before the high velocity stream reaches the wall of the target site. Positioning the openings 62 in such a fashion reduces the chance of infection, extravasation, or embolism/clot formation due to displaced plaque during dialysis.

Another preferred embodiment is directed to a distal end of a catheter portion that is made of a shape memory polymer or alloy having a temperature-based shape recovery condition. The shape recovery temperature can range from about 20° C. to about 70° C., preferably in the range of about 30° C. to about 50° C. because of the relation to body temperature. By way of example, the shape memory alloy or polymer allows for the distal end of the catheter portion to remain relatively linear for ease of insertion (i.e., when the shape recovery temperature is lower than 20° C.). When the shape recovery temperature is between 30° C. and 50° C., (i.e., after insertion into the body), the preset shape of the alloy or polymer (i.e., a spiral or loop) will be formed in the body of the patient. In an embodiment, the distal end of the catheter portion is tapered and includes a multitude of openings. In a further embodiment, the subject catheter portion incorporates or is coated with a therapeutic agent. Contemplated therapeutic agents include blood thinners such as heparin to prevent clot formation.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

I claim:

1. A safety featured dialysis needle/catheter system for preventing an inadvertent needle stick comprising:
   a housing;
   a catheter portion fixedly attached to the distal end of said housing and capable of securely transmitting fluids, wherein said catheter comprises a shape memory material having a first configuration for penetration and a second configuration acquired after penetration due to exposure to a tissue environment, wherein said second configuration comprises at least one loop, wherein each loop has a multitude of openings positioned such that they face inwardly toward the inside surface of the loop;
   a needle disposed within and manually deployable from the catheter;
   a spring positioned within the housing, having a first end connected to said housing and a second end connected to the proximal end of the needle; and
   a button for manually controlling the position of the needle relative to the catheter, comprising:
   a lock within the housing; and a stop positioned and moveable within the lock and further affixed to the needle, such that positioning of the stop distally within the lock deploys the needle outside the housing, thus biasing the spring towards the proximal end of the housing, so that when the needle is moved proximally with the stop, the spring bias will cause the needle to be retracted into and held within the catheter;
   wherein the safety feature comprises the spring, button, lock, and stop that controls the position and movement of the needle and the catheter which forms a needle guard when the needle is retracted therein.

2. The safety featured dialysis needle/catheter system according to claim 1, wherein the shape memory material is a shape memory polymer.

3. The safety featured dialysis needle/catheter system according to claim 1, wherein the shape memory material is a shape memory alloy.

4. The safety featured dialysis needle/catheter system according to claim 1, wherein the loop(s) form a shape selected from the group consisting of" a helical spiral, a pig tail, or sinusoidal wave.

5. The safety featured dialysis/catheter system according to claim 1, wherein the shape memory material has a shape recovery condition based on temperature.

6. The safety featured dialysis needle/catheter system according to claim 5, wherein the shape recovery temperature ranges from about 20° C. to about 70° C.

7. The safety featured dialysis needle/catheter system according to claim 5, wherein the shape recovery temperature ranges from about 30° C. to about 50° C., such that the catheter portion is able to be reduced in size or deformed in shape to facilitate catheter portion penetration and closing of catheter incision, prior to introduction into a body; and such that the catheter portion is able to be enlarged in size or reformed in a shape capable of maintaining the position of the catheter within a tissue or cavity after exposure to a temperature within the shape recovery temperature range so that the catheter portion can control and maintain proper fluid flow for dialysis.

8. The safety featured dialysis needle/catheter system according to claim 1, wherein the shape memory material further comprises at least one therapeutic agent.

9. The safety featured dialysis needle/catheter system according to claim 8, wherein the therapeutic agent is an anticoagulant or an agent that inhibits the development of bacterium, fungi, viruses, and other infectious agents.

10. The safety featured dialysis needle/catheter system according to claim 1, wherein a surface of the catheter portion is treated with at least one surface material.

11. The safety featured dialysis needle/catheter system according to claim 10, wherein the surface material is a hydrophilic coating to increase lubricity and facilitate insertion of the catheter portion.

12. The safety featured dialysis needle/catheter system according to claim 10, wherein the surface material is a therapeutic agent.

13. The safety featured dialysis needle/catheter system according to claim 12, wherein at least a portion of the catheter portion is transparent for viewing.

14. The safety featured dialysis needle/catheter system according to claim 13, wherein at least a portion of the catheter portion has visible markers.

15. The safety featured dialysis needle/catheter system, according to claim 1, wherein the spring is a concentric coil spring.

* * * * *